(12) United States Patent
Abrahamsson et al.

(10) Patent No.: US 7,105,823 B2
(45) Date of Patent: Sep. 12, 2006

(54) MEASURING TECHNIQUE

(75) Inventors: Christoffer Abrahamsson, Arlöv (SE); Stefan Andersson-Engels, Höör (SE); Staffan Folestad, Mölndal (SE); Jonas Johansson, Mölndal (SE); Sune Svanberg, Lund (SE)

(73) Assignee: AstraZeneca AB, Sodertalje (SE)

( * ) Notice: Subject to any disclaimer, the term of this patent is extended or adjusted under 35 U.S.C. 154(b) by 287 days.

(21) Appl. No.: 10/472,425

(22) PCT Filed: Mar. 18, 2002

(86) PCT No.: PCT/SE02/00510
§ 371 (c)(1),
(2), (4) Date: Mar. 18, 2004

(87) PCT Pub. No.: WO02/075286
PCT Pub. Date: Sep. 26, 2002

(65) Prior Publication Data
US 2004/0149914 A1    Aug. 5, 2004

(30) Foreign Application Priority Data
Mar. 21, 2001   (SE) ................................. 0101004

(51) Int. Cl.
G01J 5/02 (2006.01)
(52) U.S. Cl. .................................................... 250/343
(58) Field of Classification Search ................ 250/343, 250/339.08
See application file for complete search history.

(56) References Cited

U.S. PATENT DOCUMENTS

| | | | |
|---|---|---|---|
| 5,012,101 A * | 4/1991 | Goodall et al. ............. | 250/343 |
| 5,037,200 A | 8/1991 | Kodama | |
| 5,173,749 A * | 12/1992 | Tell et al. .................... | 356/437 |
| 5,943,122 A * | 8/1999 | Holmes ........................ | 356/73 |
| 6,040,914 A | 3/2000 | Bortz et al. | |
| 6,794,670 B1 * | 9/2004 | Folestad et al. ............. | 250/573 |
| 2001/0035957 A1 * | 11/2001 | Clermont et al. ........... | 356/451 |

FOREIGN PATENT DOCUMENTS

| WO | WO 94/21173 | 9/1994 |
|---|---|---|
| WO | WO 99/49312 | 9/1999 |
| WO | WO 01/22063 | 3/2001 |

OTHER PUBLICATIONS

Wei Wang, et al., "Femtosecond Multicolor Pump-Probe Spectroscopy of Ferrous Cytochrome c$^\dagger$," J. Phys. Chem B., vol. 104, pp. 10789-10081 (Jun. 7, 2000).

Tsuyoshi Asahi, et al., "Development of a femtosecond diffuse reflectance spectroscopic system, evaluation of its temporal resolution, and applications powder systems," Review of Scientific Instruments, vol. 69, No. 2, pp. 361-371 (Feb. 1998).

Paul Buck, et al., "Femtosecond continuum probe measurements of nonlinearities of organic dyes," SPIE, vol. 2853, pp. 12-19 (1996).

Gerd Scheitzer, et al., "Femtosecond Transient Absorption Spectoscopy Using Multichannel Detection and Tunable UV Pump Light," Soc. Opt. & Quant.Electron; Proc. Int. Conf. on Lasers '98, Tucson, Arizona, pp. 129-136 (Dec. 7-11, 1998).

* cited by examiner

*Primary Examiner*—David Porta
*Assistant Examiner*—Christopher Webb
(74) *Attorney, Agent, or Firm*—Fish & Richardson P.C.

(57) ABSTRACT

The present invention relates to apparatuses for use in performing a quantitative analysis of a turbid pharmaceutical sample, e.g. a tablet, a capsule or a similar sample forming a pharmaceutical dose. A pharmaceutical, turbid sample (24, 57, 67) is irradiated with an excitation beam (20, 53, 64) of radiation, e.g. near infrared radiation. The intensity of emitted radiation (30) from the sample (24, 57, 67) is detected as function of both the wavelength of the emitted radiation and the photon propagation time through said sample (24, 57, 67). Optionally, the intensity of the emitted radiation (30) from the sample (24, 57, 67) is also detected in a spatially resolved manner.

39 Claims, 9 Drawing Sheets

MEASURING TECHNIQUE

FIELD OF THE INVENTION

The present invention relates to apparatuses for analysing a turbid pharmaceutical sample, e.g. a tablet, a capsule—especially a multiple unit pellet system (MUPS)—or a similar sample forming a pharmaceutical dose.

BACKGROUND OF THE INVENTION

Non-invasive, non-destructible analysis of whole tablets can be carried out by means of near-infrared (NIR) or Raman spectrometry. Today, NIR spectroscopy is a recognised technique for performing a fast analysis of compounds. The common feature of both these techniques is that they utilise light in the NIR wavelength region (700–2500 nm, specifically 700–1500 nm) where pharmaceutical tablets are relatively transparent (low molar absorptivity). That is, light can in this region penetrate compressed powders several mm:s why information in the content can be obtained emanating from the bulk of the tablet and not only from the surface. A practical advantage of using NIR radiation is that diode lasers can be used.

One example of such an analysis is described in U.S. Pat. No. 5,760,399, assigned to Foss NIRsystems Inc. This document discloses an instrument for performing a NIR spectrographic transmission measurement of a pharmaceutical tablet. This instrument is, however, capable of providing only limited information as to the content of a sample, typically the quantity of a particular component in a sample. This prior-art instrument cannot provide detailed information of, for example, the three-dimensional distribution of one or more components in a sample. The technical background on which this limitation is based will be further discussed in connection with the description of the present invention.

The prior art also includes a significant amount of methods for optical imaging of human tissues, in particular for detecting disturbances of homogeneity, such as the presence of a tumour in human tissue. These methods are generally qualitative measurements, not quantitative, in the sense that they primarily focus on determining the presence and the location of an inhomogeneity. These prior-art methods are not suitable for performing a quantitative analysis on pharmaceutical, turbid samples, such as tablets and capsules, in order to determine e.g. content and structural parameters.

SUMMARY OF THE INVENTION

According to a first aspect of the invention there is provided apparatuses for use in quantitative analysis of a turbid, pharmaceutical sample, in particular a pharmaceutical tablet or capsule of an equivalent pharmaceutical dose.

According to the invention, the apparatuses comprises:
  means for generating an excitation beam of radiation; and
  means for focusing said excitation beam onto said sample.

According to one embodiment the apparatus also comprises:
  means for intensity modulating said excitation beam; and
  means for detecting all wavelengths simultaneously.

According to another embodiment the apparatus also comprises:
  means for splitting said excitation beam into two beams (70, 74); and
  means (68, 71) for detecting transmitted light and non-transmitted light respectively.

The invention is based on the following principles. A sample to be analysed by a spectrometric transmission and/or reflection measurement presents a number of so called optical properties. These optical properties are (i) the absorption coefficient, (ii) the scattering coefficient and (iii) the scattering anisotropy. Thus, when the photons of the excitation beam propagate through the turbid sample—in transmission and/or reflective mode—they are influenced by these optical properties and, as a result, subjected to both absorption and scattering. Photons that by coincidence travel along an essentially straight path through the sample and thus do not experience any appreciable scattering will exit the sample with a relatively short time delay. Photons that are directly reflected on the irradiated surface will also present a relatively short time delay, in the case of measurements on reflected light. On the other hand, highly scattered photons (transmitted and/or reflected) exit with a substantial time delay or phase difference. This means that all these emitted photons—presenting different propagation times—mediate complementary information about the sample.

In a conventional steady state (no time-resolution) measurement, some of that complementary information is added together since the emitted light is captured by a time-integrated detection. Accordingly, the complementary information is lost in a conventional technique. For instance, a decrease in the registered light intensity may be caused by an increase in the sample scattering coefficient. However, the information about the actual cause is hidden, since all the emitted light has been time-integrated.

According to the invention and in contrast to such prior-art NIR spectroscopy with time-integrated intensity detection, the intensity of the emitted radiation from the sample is measured both as a function of the wavelength and as a function of the photon propagation time through said sample. Thus, the inventive method can be said to be both wavelength-resolved and time-resolved. It is important to note that the method is time-resolved in the sense that it provides information about the kinetics of the radiation interaction with the sample. Thus, in this context, the term "time resolved" means "photon propagation time resolved". In other words, the time resolution used in the invention is in a time scale which corresponds to the photon propagation time in the sample (i.e. the photon transit time from the source to the detector) and which, as a consequence, makes it possible to avoid time-integrating the information relating to different photon propagation times. As an illustrative example, the transit time for the photons may be in the order of 0, 1–2 ns. Especially, the term "time resolved" is not related to a time period necessary for performing a spatial scanning, which is the case in some prior-art NIR-techniques where "time resolution" is used.

As a result of not time-integrating the radiation (and thereby "hiding" a lot of information) as done in the prior art, but instead time resolving the information from the excitation of the sample in combination with wavelength resolving the information, the invention makes it possible to establish quantitative analytical parameters of the sample, such as content, concentration, structure, homogeneity, etc.

Both the transmitted radiation and the reflected radiation from the irradiated sample comprise photons with different time delay. Accordingly, the time-resolved and wavelength resolved detection may be performed on transmitted radiation only, reflected radiation only, as well as a combination of transmitted and reflected radiation.

The excitation beam of radiation used in the present invention may include infrared radiation, especially near infrared radiation (NIR) in the range corresponding to wavelengths of from about 700 to about 1700 nm, particularly form 700 to 1300 nm. However, the excitation beam of radiation may also include visible light (400 to 700 nm) and UV radiation. In this connection, it should also be stated that the term "excitation" should be interpreted as "illumination", i.e. no chemical excitation of the sample is necessary.

Preferably, the step of measuring the intensity as a function of photon propagation time is performed in time-synchronism with the excitation of the sample. In a first preferred embodiment, this time synchronism is implemented by using a pulsed excitation beam, presenting a pulse train of short excitation pulses, wherein each excitation pulse triggers the intensity measurement. To this end, a pulsed laser system or laser diodes can be used. This technique makes it possible to perform a photon propagation time-resolved measurement of the emitted intensity (transmitted and/or reflected) for each given excitation pulse, during the time period up to the subsequent excitation pulse.

In order to avoid any undesired interference between the intensity measurements relating to two subsequent pulses, such excitation pulses should have a pulse length short enough in relation to the photon propagation time in the sample and, preferably, much shorter than the photon propagation time.

To summarise, in this embodiment of the invention the intensity detection of the emitted radiation associated with a given excitation pulse is time-synchronised with this pulse, and the detection of the emitted light from one pulse is completed before next pulse.

The data evaluation can be done in different ways. By defining the boundary conditions and the optical geometry of the set-up, iterative methods such as Monte Carlo simulations can be utilised to calculate the optical properties of the sample and indirectly content and structural parameters. Alternatively, a multivariate calibration can be used for a direct extraction of such parameters. In multivariate calibration, measured data is utilised to establish an empirical mathematical relationship to the analytical parameter of interest, such as the content or structure of a pharmaceutical substance. When new measurements are performed, the model can be used to predict the analytical parameters of the unknown sample.

In an alternative embodiment the radiation source is intensity modulated in time. Then, frequency domain spectroscopy can be used for determining phase shift and/or modulation depth of the emitted radiation from the sample. Thus, the phase and/or modulation depth of the emitted sample radiation is compared with those of the excitation radiation. That information can be used to extract information about the time delay of the radiation in the sample. Moreover, the emitted radiation can be measured for a multitude of wavelengths to obtain spectral information. It should be noted that the above mentioned frequency domain spectroscopy is also a "time-resolved" technique according to the invention, since it also provides information about the kinetics of the photon interaction with the sample. With similar mathematical procedures as above, the same quantitative analytical information can be extracted.

A pulsed excitation beam according to the first embodiment, and an intensity modulated excitation beam according to the second embodiment, share the common feature that they make it possible to identify—in said excitation beam—a specific "excitation time point" which can be used to trigger the detection of the emitted radiation from the sample, i.e. to time-synchronise the time-resolved detection with the excitation of the sample. This can be performed by letting the pulsed or modulated beam trigger a photodetector or the equivalent, which in its turn triggers the detection unit via suitable time-control circuitry.

The time detection may be implemented by the use of a time-resolved detector, such as a streak camera. It may also be implemented by the use of a time-gated system, by which the detection of emitted radiation is performed during a limited number of very short time slices instead of the full time course. The time length of each such time slice is only a fraction of the detection time period during which the time resolved detection is performed for each excitation. By measuring several such "time slices" a coarse time resolution is achieved. An attractive alternative is to measure wavelength resolved spectra at two such time gates, prompt light and delayed light. Furthermore, time-resolved data may be recorded by means of other time-resolved equipment, transient digitizers or equivalent.

In a further embodiment a Fourier transform detector is used, whereby a mirror is scanned back and forth producing an interferogram. The interferogram will contain information about the light transmitted through the sample at all wavelengths. Since an interferogram is used, all wavelengths are monitored simultaneously. The result will be a spectrum of the transmitted light. The light source is intensity modulated with a modulation driver at high frequency (MHz-GHz). The phase and the modulation depth of the detected signal and the modulation driver are compared and used as output signals. These will provide information about the time behaviour of the photon propagation through the sample. If the scanning speed of the moving mirror of the Fourier spectrometer is much slower than the light modulation frequency, a value for the phase difference and the modulation depth is obtained for each position of the moving mirror. Thus, the phase difference and the modulation depth are measured by a scan in the Fourier space and not a scan in the wavelength domain. Information about physically relevant parameters, such as contents or particle size, of the sample can be extracted by deconvolution techniques and chemometric models. A multitude of modulation frequencies can be utilised for more accurate analysis.

In yet a further embodiment intensity modulated light is directed onto a sample. The transmitted or diffusely reflected light is detected by a fast detector and a second detector detects the light before irradiating the sample. The signals from the two detectors are compared regarding the phase difference and modulation depth. These two values are registered for each wavelength in sequence and from these values information about, for example, contents can be extracted with deconvolution techniques and chemometric models.

The wavelength resolved detection may be implemented in many different, conventional ways. It may be implemented by the use of a multi-channel detector, such as microchannel plate or a streak camera. Use can be made of light dispersive systems, such as (i) a spectrometer, (ii) a wavelength dependent beam splitter, (iii) a non-wavelength dependent beam splitter in combination with a plurality of filters for filtering each of respective components for providing radiation of different wavelength or wavelength band, (iv) a prism array or a lens system separating the emitted radiation from the sample into a plurality of components in combination with a plurality of filters, etc.

DESCRIPTION OF THE DRAWINGS

The above and other features and advantages of the invention are defined in the claims and described in greater detail below with reference to the accompanying drawings, which illustrate preferred embodiments.

FIG. 3b is a 3D plot of the streak camera image in FIG. 3a.

FIG. 4b is a 3D plot of the streak camera image in FIG. 4a.

DESCRIPTION OF PREFERRED EMBODIMENTS

Figure 1A:
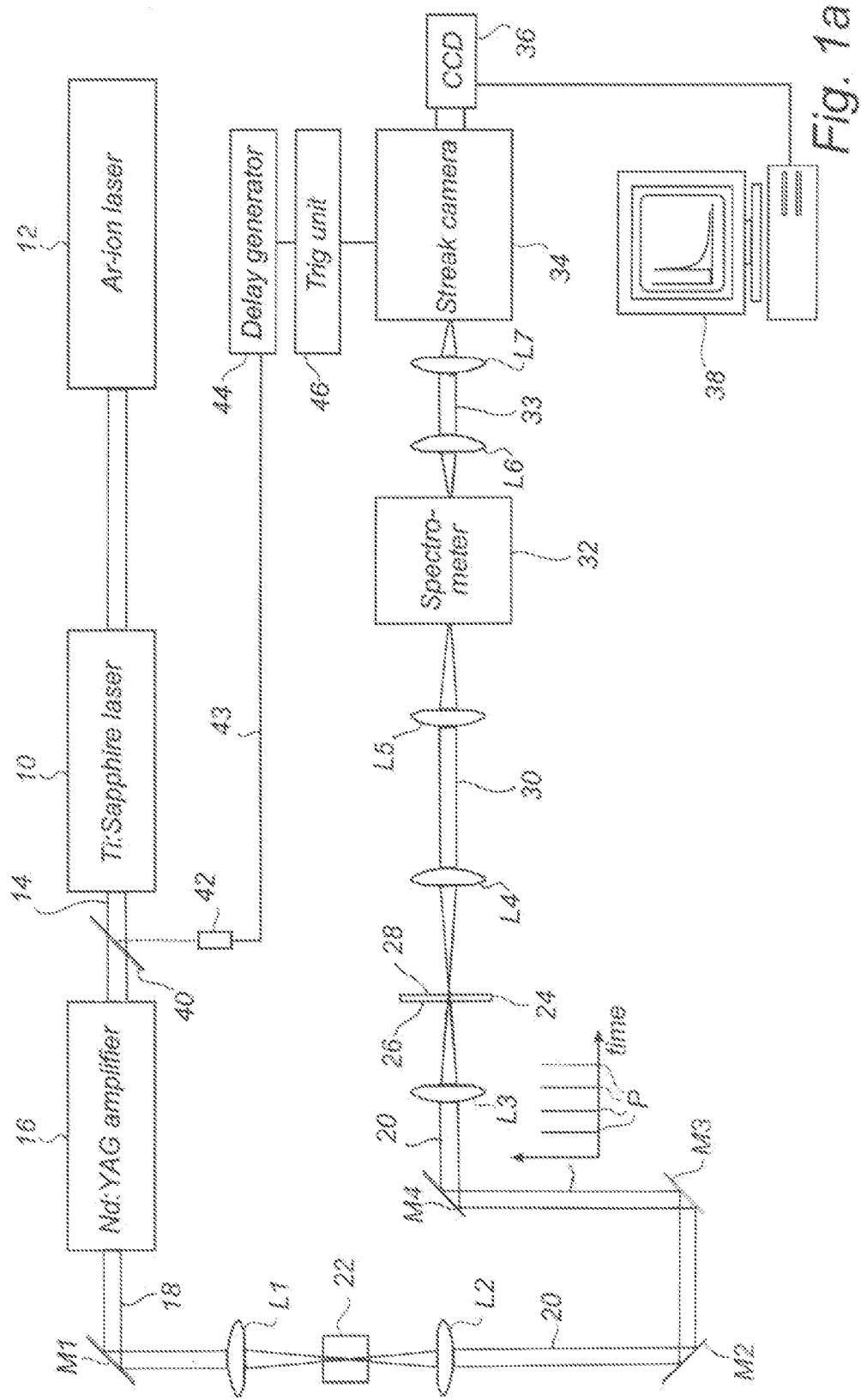
FIG. 1a illustrates a set-up for performing a time-resolved and wavelength resolved analysis.

Referring now to FIG. 1a, an apparatus according to a first embodiment for performing a time-resolved analysis according to the invention comprises a Ti:sapphire laser 10 pumped by an argon laser 12. The laser beam 14 thereby generated is amplified by a neodymium YAG amplifier stage 16 into an amplified laser beam 18. In order to create an excitation beam 20 of "white" light, the laser beam 18 is passed through a water filled cuvette 22 via a mirror M1 and a first lens system L1.

A sample to be analysed is schematically illustrated at reference numeral 24 and comprises a front surface 26 and a back surface 28. The sample 24 is temporarily fixed in a sample-positioning unit (not shown). The excitation laser beam 20 is focused onto the front surface 26 of sample 24 via a lens system L2/L3 and mirrors M2-M4. On the opposite side of sample 24, the transmitted laser beam 30 is collected from the backside by lens system L4/L5 and focused into spectrometer 32. In the illustrated set-up, the sample 24 may be a pharmaceutical, solid tablet having a diameter of e.g. 9 mm. The excitation beam 20 may be focused in a spot of about 1 mm. In other embodiments, the excitation beam may be focused on the whole sample, or scanned over the sample.

In an alternative embodiment the apparatus is attached to for example a fluidised bed for remote sampling of a selected part of the contents in the bed.

As schematically illustrated in FIG. 1a, the excitation beam 20 in this embodiment is time-pulsed into a pulse train of short, repetitive excitation pulses P. The pulse length of each excitation pulse P is short enough and the time spacing between two consecutive excitation pulses P is long enough in relation to the transit time of the beam (i.e. in relation to the time taken for each pulse to be completely measured in time), such that any interference is avoided between the detected-light from one given excitation pulse $P_n$ and the detected light from the next excitation pulse $P_{n+1}$. Thereby, it is possible to perform a time-resolved measurement on the radiation from one excitation pulse P at a time.

From the spectrometer 32, the detected light beam 33 is passed via lens system L6/L7 to a time-resolved detection unit, which in this embodiment is implemented as a streak camera 34. The streak camera 34 used in an experimental set-up according to FIG. 1a was a Hamamutsu Streak Camera Model C5680. Specifically, the streak camera 34 has an entrance slit (not shown) onto which the detected light beam 33 from the spectrometer 32 is focused. It should be noted that only a fraction of the light emitted from the sample is actually collected in the spectrometer 32 and, thereby, in the detection unit 34. As a result of passing through the spectrometer 32, the emitted radiation 30 from the sample 24 is spectrally divided in space, such that radiation received by the streak camera 34 presents a wavelength distribution along the entrance slit.

The incident photons at the slit are converted by the streak camera into photoelectrons and accelerated in a path between pairs of deflection plates (not shown). Thereby, the photoelectrons are swept along an axis onto a microchannel plate inside the camera, such that the time axis of the incident photons is converted into a spatial axis on said microchannel plate. Thereby, the time in which the photons reached the streak camera and the intensity can be determined by the position and the luminance of the streak image. The wavelength-resolution is obtained along the other axis. The photoelectron image is read out by a CCD device 36, which is optically coupled to the streak camera 34. The data collected by the CCD device 36 is coupled to an analysing unit 38, schematically illustrated as a computer and a monitor.

In the set-up in FIG. 1a, the intensity of the emitted light is measured as a function of time in time-synchronism with each excitation of the sample. This means that the detection unit comprising the streak camera 34 and the associated CCD device 36 is time-synchronised with the repetitive excitation pulses P. This time-synchronism is accomplished as follows: each excitation pulse P of the laser beam 14 triggers a photodetector 42 or the equivalent via an optical element 40. An output signal 43 from the photodetector 42 is passed via a delay generator 44 to a trig unit 46, providing trig pulses is to the streak camera 34. In this manner, the photon detection operation of the streak camera is activated and de-activated at exact predetermined points in time after the generation of each excitation pulse P.

As mentioned above, the evaluation and analysis of the collected, time-resolved information can be done in different ways. As schematically illustrated in FIG. 1a, the collected data information from each excitation is transferred from the streak camera 34 and the CCD device 36 to a computer 38 for evaluation of the information. Monte Carlo simulations, multivariate calibrations, etc as mentioned in the introductory part of this application can be utilised in order to calculate the optical properties of the sample and, indirectly, content and structural parameters of the sample 24.

Figure 1B:
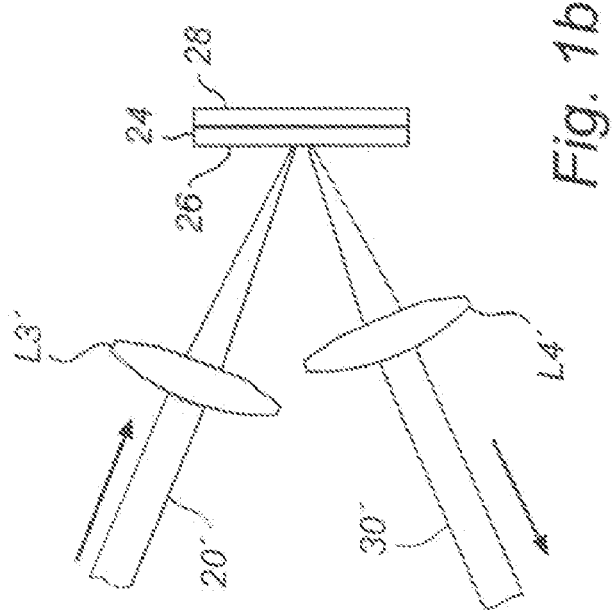
FIG. 1b illustrates an embodiment where the excitation and the collection of emitted light are performed at the irradiation side only of the sample.

In the embodiment shown in FIG. 1b, it is the transmitted radiation—the beam 30—which is detected in a time-resolved manner. However, the invention can also be implemented by detecting the radiation reflected from the sample. FIG. 1b schematically illustrates how an excitation beam 20' corresponding to excitation beam 20 in FIG. 1a is focused via a lens L3' onto the front surface 26 of a sample 24. The photons of each excitation pulse will be reflected both as directly reflected photons from the front surface 26 as well as diffusely backscattered photons with more or less time delay. This directly reflected radiation as well as the diffusely backscattered radiation is collected by a lens L4' into a detection beam 30', corresponding to detection beam 30 in FIG. 1a.

As stated above, it is possible to combine the embodiments illustrated in FIGS. 1a and 1b into one single embodiment, where both transmitted and backscattered light is detected and analysed in a time-resolved and wavelength-resolved manner according to the invention.

Figure 2:
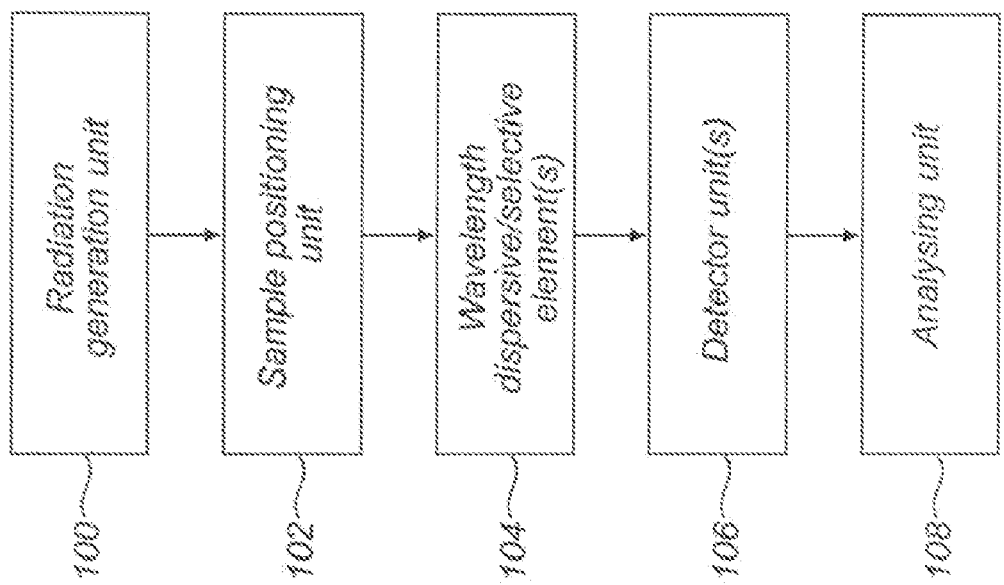
FIG. 2 illustrates functional components for implementing the present invention.

FIG. 2 schematically discloses the main functional components in an embodiment for implementing the inventive method, including a radiation generation unit 100 (components 10, 12 and 16 in FIG. 1a), a sample positioning unit 102, one or more wavelength dispersive/selective elements 104 (component 32 in FIG. 1a), one or more detector units 106 (components 34 and 36 in FIG. 1a) and an analysing unit 108 (component 38 in FIG. 1a).

Figure 3A:
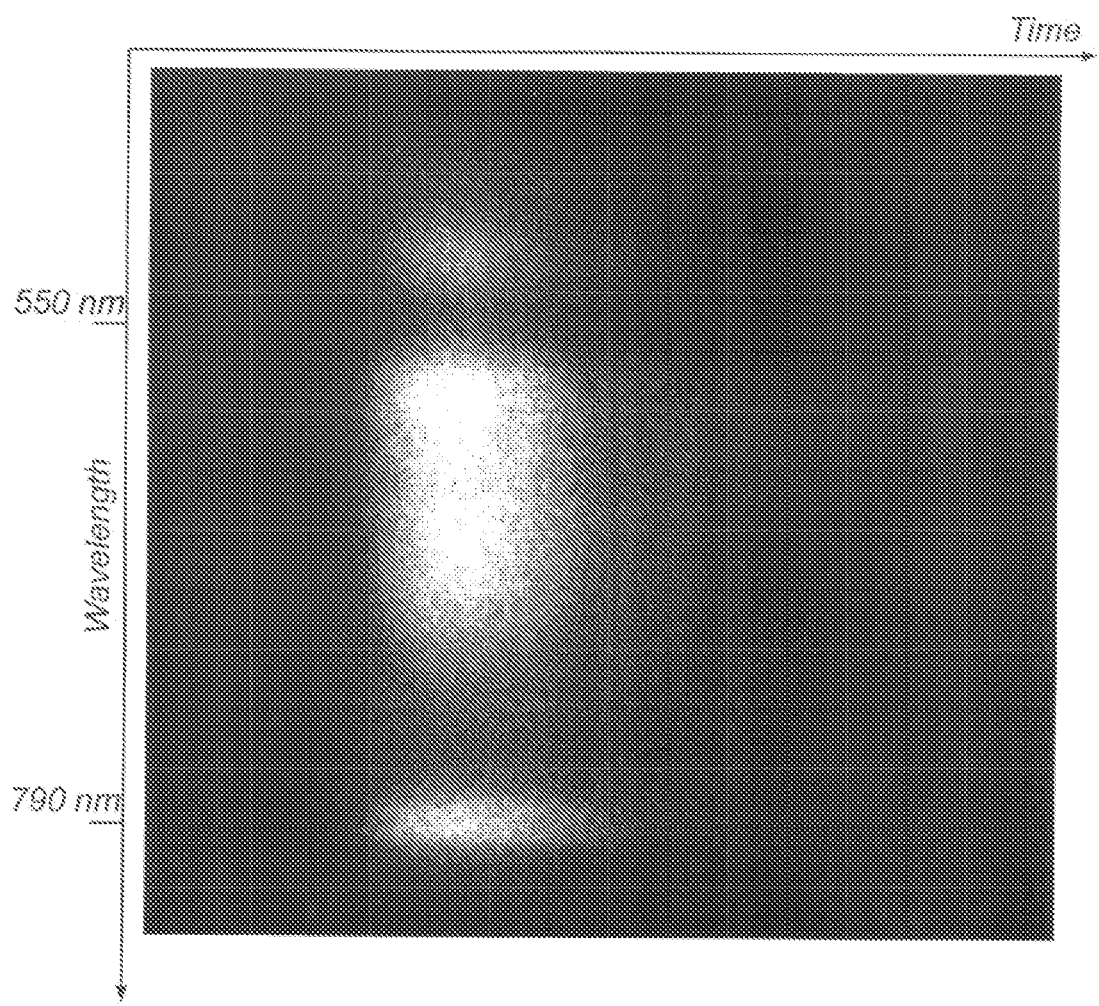
FIG. 3a is a streak camera image, illustrating an experimental result of a wavelength-resolved and time-resolved tablet transmission measurement according to the invention.
Figure 3B:
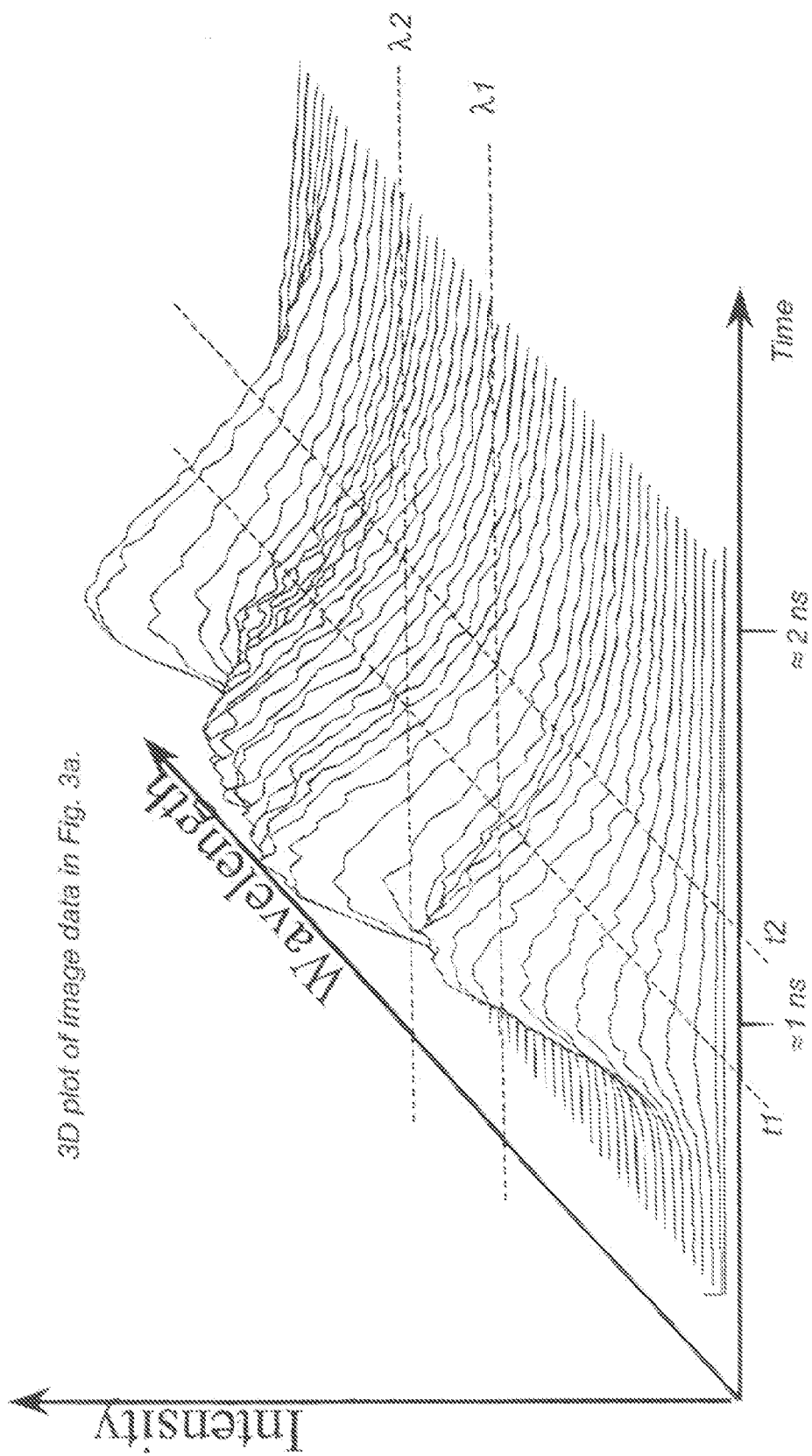

The water filled cuvette 22 producing white laser light in combination with the spectrometer 32 acting as a wavelength-dispersive element makes it possible to collect data that is both wavelength-resolved and time-resolved. FIGS. 3a and 3b illustrate the experimental result of such a detection. It should be noted that the time scale in both FIG. 3a and FIG. 3b illustrate the intensity variation over time for one pulse only, although the actual data used for producing these figures is based in accumulated data from many readings. The time axis in FIGS. 3a and 3b is in nano second scale.

FIG. 3a illustrates a streak camera image pasted into a time-wavelength diagram, the light portions correspond to high intensity values. The left part of the image corresponds to detected photons having a relatively short time delay, whereas the right part of the image corresponds to photons with a relatively long delay time.

The 3D plot in FIG. 3b corresponds to the image in FIG. 3a. This 3D plot clearly illustrates how the time-resolved spectroscopy according to the invention results in an intensity measurement as a function of both wavelength and photon propagation time. This 3D plot also clearly illustrate that the total information content as obtained by the present invention is significantly greater than the information obtainable with a conventional time-integrated detection.

In FIG. 3b, for each wavelength (such as for the wavelengths λ1 and λ2 as identified in FIG. 3b) there is a multitude of timely spaced intensity readings. Thus, for each wavelength it is possible to obtain a full curve of emitted (transmitted and/or reflected) intensity vs. propagation time. The form of these "time profiles" shown in FIG. 3b is dependent on the relation between the optical properties of the analysed sample. With such a time-resolved and wavelength-resolved spectroscopy, it is possible to obtain information for describing the light interaction with the sample. As an example, this provides the basis-for determining an analytical concentration in a sample that is proportional to the absorption coefficient but not related to the scattering. As another example, one might want to measure an analytical quantity that correlates to the scattering properties of the sample instead.

As illustrated by the dashed lines t1 and t2 in FIG. 3b, it is also possible to evaluate the emitted light by detecting the intensity during fixed time slices. This would give a more coarse time resolution. In one embodiment, wavelength-resolved spectra are measured at two time gates only—one for "prompt" light and one for "delayed" light.

Figure 5:
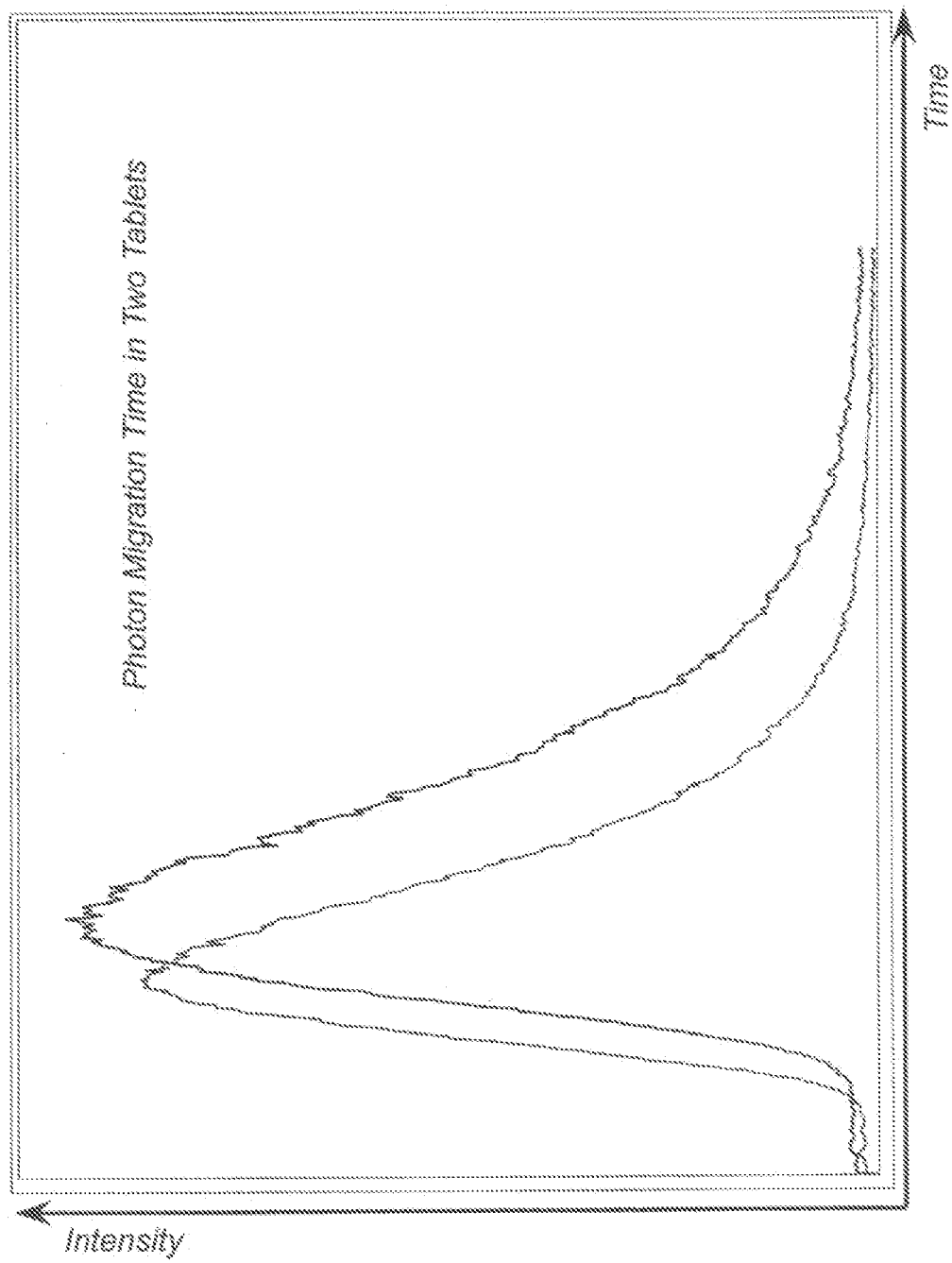
FIG. 5 is diagram illustrating experimental results from transmission measurements on two different tablet samples.

The intensity-time diagram in FIG. 5 illustrates two experimental, time-resolved results from measurements on two different tablets. By selecting suitable time gates where the difference is substantial, one can easily distinguish different tablets from each other.

As an alternative to the set-ups illustrated in FIGS. 1a and 1b, instead of using the water cuvette 20 in combination with the spectrometer 32, it is possible to use wavelength selective light sources, such as diode lasers. On the detector side, wavelength selective detectors, such combinations of filters and detector diodes, can be used for each wavelength.

Figure 4A:
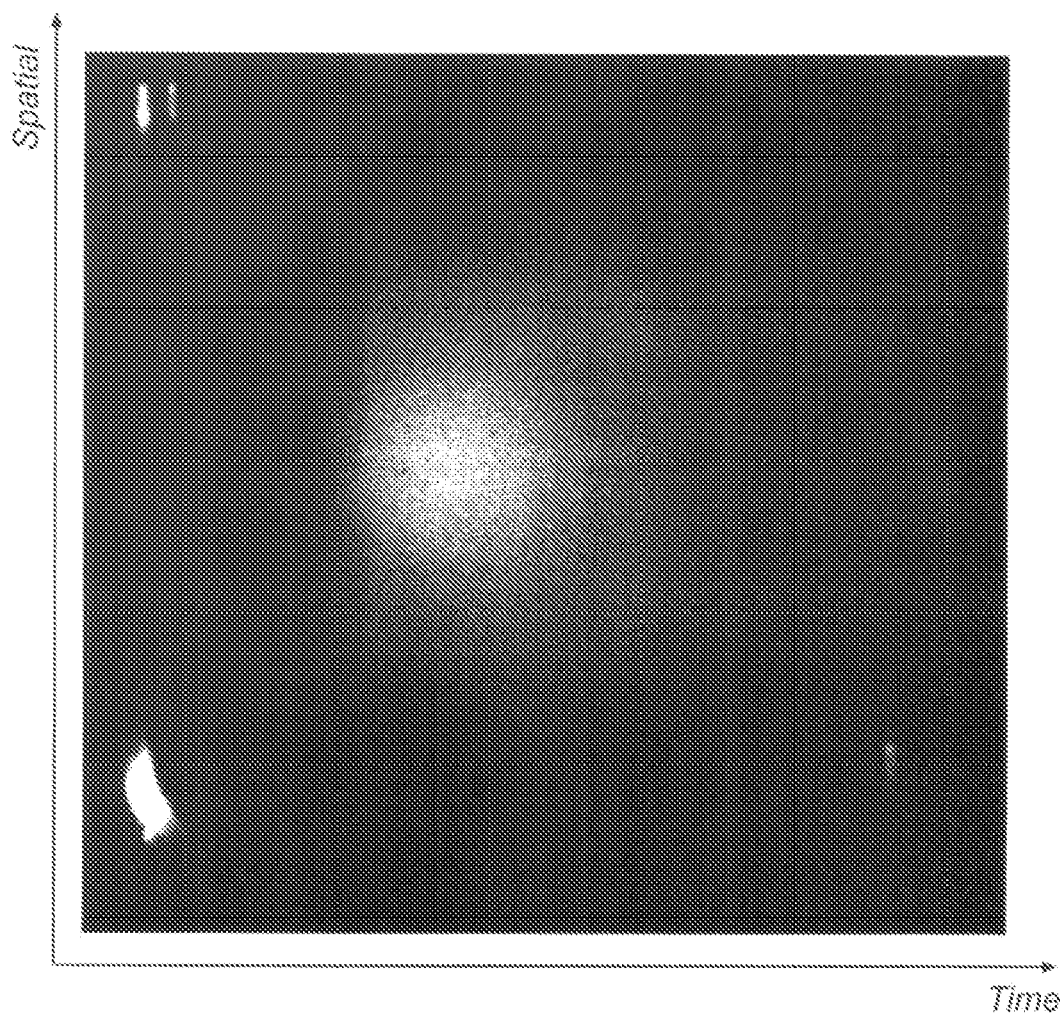
FIG. 4a is a streak camera image, illustrating an experimental result of a time-resolved tablet transmission measurement according to the invention, in combination with spatial resolution.
Figure 4B:
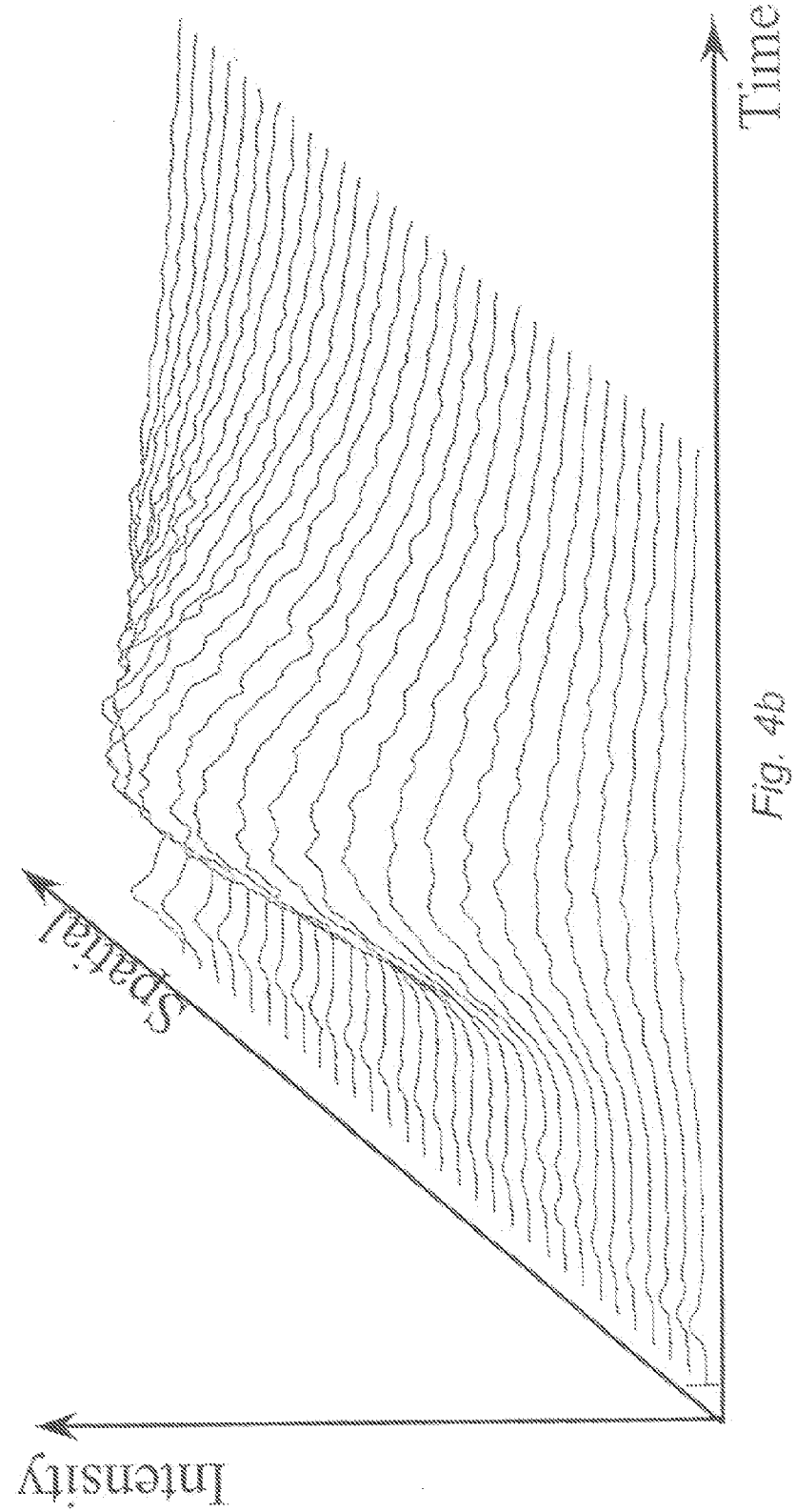

It is possible to combine the invention with spatial-resolved intensity detection on the emitted light from the sample. In this context, the term "spatial resolved" refers to a spatial resolution obtained for each excitation pulse. Especially, "spatial resolved" does not refer to a spatial resolution based on a scanning in time of the excitation beam in relation to the sample. As an illustrative example, by removing the water cuvette 22 and the spectrometer 32 in the FIG. 1a set-up, the light focused on the entrance slit of the streak camera would be spatial resolved along the slit, corresponding to a "slit" across the sample. A streak camera image obtained by such a set-up is illustrated in FIG. 4a, and a corresponding 3D plot is illustrated in FIG. 4b. In accordance with FIGS. 3a and 3b discussed above, FIGS. 4a and 4b represent one pulse only; i.e. the spatial resolution illustrated does not correspond to any scanning of the excitation beam over the sample.

Figure 6:
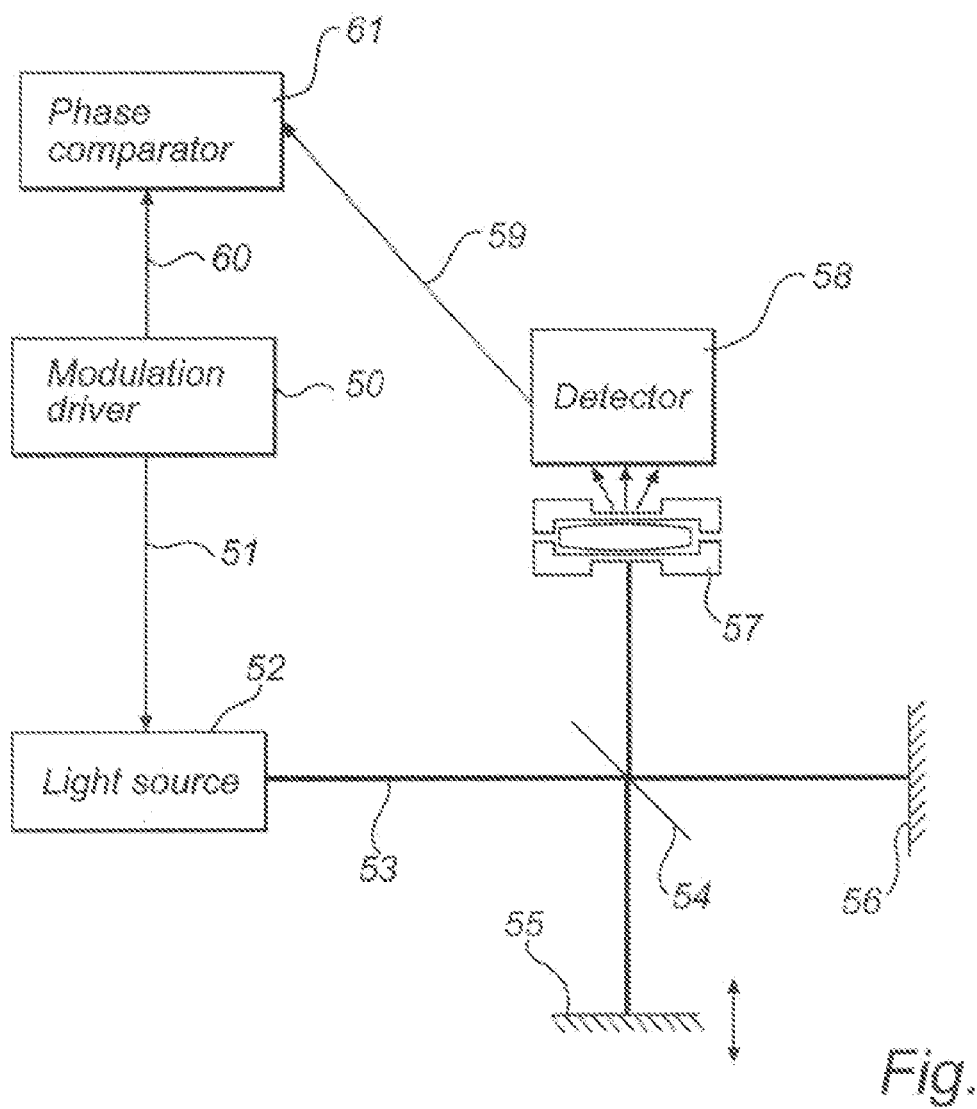
FIG. 6 illustrates an alternative set-up for performing a time-resolved and wavelength resolved analysis.

A further alternative set-up is illustrated in FIG. 6. A modulation driver 50 intensity modulates 51 a light source 52. The light source is intensity modulated with a high frequency (MHz-GHz). The light source 52, preferably a light emitting diode (LED), emits an excitation beam 53 in broad range of wavelengths. The excitation beam 53 reaches a beam splitter 54 where the excitation beam 53 is divided. One part of the excitation beam 53 continues towards a mirror 56 where it is reflected back to the beam splitter 54. The other part of the excitation beam 53 continues towards a moving mirror 55 where it is reflected back to the beam splitter 54. The two parts of the split excitation beam 53 are brought together again at the beam splitter 54 where they continue towards the sample 57. The sample 57 is thus irradiated and the transmitted light detected by a detector 58. By scanning the moving mirror 55 back and forth, an interferogram is produced. This interferogram contains information about the light transmitted through the sample at all wavelengths. By using an interferogram all wavelengths are monitored simultaneously and the result will be a spectrum of the transmitted light intensity. The signal 60 from the modulation driver 50 is compared to the signal 59 from the detector 58 by a phase comparator 61. From the comparison in the comparator 61 information can be extracted with deconvolution techniques and chemometric models.

Figure 7:
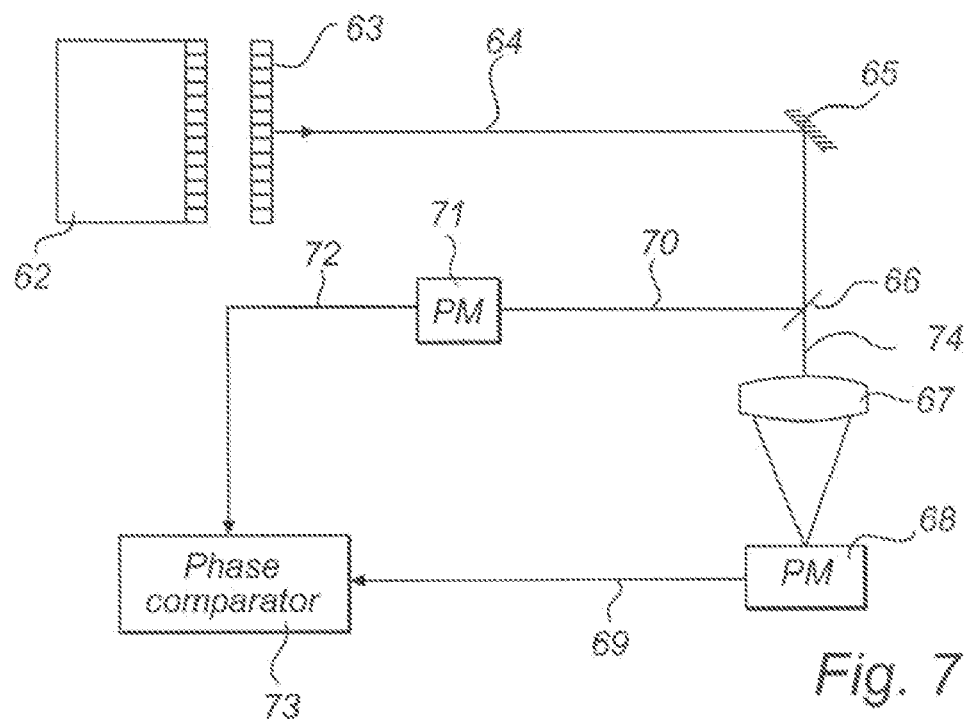
FIG. 7 illustrates yet another alternative set-up for performing a time-resolved and wavelength resolved analysis.
Figure 8:
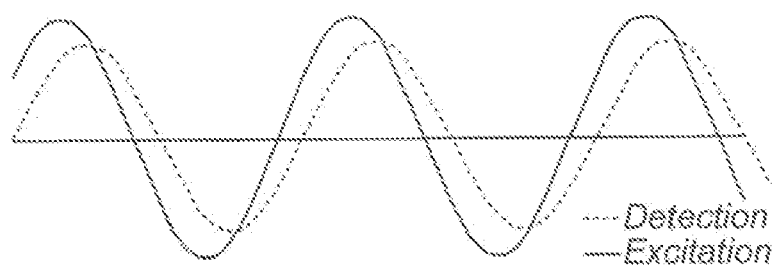
FIG. 8 is a diagram illustrating experimental results from measurements made with the set-up in FIG. 7.

A further alternative set-up of the present invention is illustrated in FIG. 7. In this embodiment the light source producing intensity modulated light is made up of an array of diode lasers 62. The array of diode lasers 62 covers a wide range of wavelengths and a multiplexer 63 is used to scan the various diode lasers 62 in the array, i.e. the multiplexer 63 executes the scan through the different wavelengths. The produced excitation beam travels through a set of mirrors, illustrated in FIG. 7 with one mirror 65, until it reaches a beam splitter 66 where the excitation beam 64 is divided up into two beams 70 and 74. One beam 74 irradiates the sample 67 and the transmitted light is detected by a photomultiplier 68. The other beam 70 is directed directly to a photomultiplier 71 without irradiating the sample 67. The two signals 69 and 72 produced by the photomultipliers 68 and 71 due to is the incident beams are compared in a phase comparator 73. These two signals 69 and 72 are recorded for each wavelength in sequence according to the scanning of the diode laser array 62 by the multiplexer 63. The diagram in FIG. 8 shows an example of the two signals 69 and 72 where the excitation sinus curve corresponds to the beam 70 detected by photomultiplier 71 in FIG. 7, i.e. the beam unaffected by the sample 67. The beam 74, after irradiating the sample, is the detection sinus curve in FIG. 8. Information about physical parameters of the sample can be extracted from the type of diagram illustrated in FIG. 8 by comparing the two sinus shapes.

In either of the above embodiments the measurements can be carried out by remote sampling, i.e. the sample does not have to be positioned in specific means. Therefore, the apparatuses can be placed to measure the contents in a turbid, pharmaceutical sample flow and not only in a specifically selected sample, e.g. a tablet or a capsule.

The foregoing is a disclosure of preferred embodiments for practicing the present invention. However, it is apparent that device incorporating modifications and variations will be obvious to one skilled in the art. Inasmuch as the foregoing disclosure is intended to enable one skilled in the art to practice the instant invention, it should not be construed to be limited thereby, but should be construed to include such modifications and variations as fall within its true spirit and scope.

The invention claimed is:

1. An apparatus for use in quantitative analysis of a turbid pharmaceutical sample, comprising:
    means for generating an excitation beam of radiation comprising an intensity modulated light emitting diode (LED);
    means for intensity modulating said excitation beam;
    means for focusing said excitation beam onto said sample; and
    means for detecting all wavelengths simultaneously.

2. An apparatus as claimed in claim 1, wherein said means for detecting comprises a time-resolved detection unit.

3. An apparatus as claimed in claim 1, wherein said means for detecting comprises a phase-resolved detection unit.

4. An apparatus as claimed in claim 1, wherein said means for detecting comprises a time-grated system.

5. An apparatus as claimed claim 1, further comprising means for performing a spatial-resolved detection of said intensity.

6. An apparatus as claimed in claim 1, wherein said pharmaceutical, turbid sample is a solid sample, in particular a tablet, a capsule, a bulk powder or an equivalent pharmaceutical dose.

7. An apparatus as claimed in claim 1, wherein said pharmaceutical, turbid sample is a dispersion.

8. An apparatus as claimed in claim 1, wherein the excitation beam comprises infrared radiation.

9. An apparatus as claimed in claim 8, wherein the infrared radiation is in the near infrared radiation (NIR).

10. An apparatus as claimed in claim 1, wherein the radiation has a frequency in the range corresponding to wavelengths from about 700 to about 1700 nm, particularly 700 to 1300 nm.

11. An apparatus as claimed in claim 1, wherein the excitation beam comprises visible light.

12. An apparatus as claimed in claim 1, wherein the excitation beam comprises UV radiation.

13. An apparatus as claimed in claim 1, wherein said means for generating an excitation beam of radiation comprises one or more diode lasers.

14. An apparatus as claimed in claim 1, wherein said means for generating an excitation beam of radiation comprises an intensity modulated lamp.

15. An apparatus as claimed in claim 1, wherein said means for intensity modulating said excitation beam is a modulation driver.

16. An apparatus as claimed in claim 1, wherein said means for focusing the excitation beam on a sample are parts of a Fourier spectrometer.

17. An apparatus as claimed in claim 15, wherein a phase comparator is arranged to compare signals from the modulation driver and from the means for detecting.

18. An apparatus as claimed in claim 1, comprising means for positioning a turbid pharmaceutical sample.

19. An apparatus for use in quantitative analysis of a turbid pharmaceutical sample, comprising:
    means for generating an excitation beam of radiation comprising an intensity modulated light emitting diode (LED);
    means for focusing said excitation beam onto said sample;
    means for splitting said excitation beam into two beams; and
    means for detecting transmitted light and non-transmitted light respectively.

20. An apparatus as claimed in claim 19, wherein said means for detecting comprises a time-resolved detection unit.

21. An apparatus as claimed in claim 19, wherein said means for detecting comprises a phase-resolved detection unit.

22. An apparatus as claimed in claim 19, wherein said means for detecting comprises a time-grated system.

23. An apparatus as claimed in claim 19, further comprising means for performing a spatial-resolved detection of said intensity.

24. An apparatus as claimed in claim 19, wherein said pharmaceutical, turbid sample is a solid sample, in particular a tablet, a capsule, a bulk powder or an equivalent pharmaceutical dose.

25. An apparatus as claimed in claim 19, wherein said pharmaceutical, turbid sample is a dispersion.

26. An apparatus as claimed in claim 19, wherein the excitation beam comprises infrared radiation.

27. An apparatus as claimed in claim 26, wherein the infrared radiation is in the near infrared radiation (NIR).

28. An apparatus as claimed in claim 19, wherein the radiation has a frequency in the range corresponding to wavelengths from about 700 to about 1700 nm, particularly 700 to 1300 nm.

29. An apparatus as claimed in claim 19, wherein the excitation beam comprises visible light.

30. An apparatus as claimed in claim 19, wherein the excitation beam comprises UV radiation.

31. An apparatus as claimed in any claim 19, wherein said means for generating an excitation beam of radiation comprises one or more diode lasers.

32. An apparatus as claimed in claim 19, wherein said means for generating an excitation beam of radiation comprises an intensity modulated lamp.

33. An apparatus as claimed in claim 19, wherein said means for generating an excitation beam of radiation is an array of diode lasers and a multiplexer.

34. An apparatus as claimed in claim 19, wherein said means for detecting transmitted light and non-transmitted light are photomultipliers.

35. An apparatus as claimed in claim 19, wherein a phase comparator is arranged to compare the signals from said means for detecting transmitted light and non-transmitted light.

36. An apparatus for use in quantitative analysis of a turbid pharmaceutical sample, comprising:
- means for generating an excitation beam of radiation;
- means for intensity modulating said excitation beam comprising a modulation driver;
- means for focusing said excitation beam onto said sample; and
- means for detecting all wavelengths simultaneously.

37. An apparatus for use in quantitative analysis of a turbid pharmaceutical sample, comprising:
- means for generating an excitation beam of radiation;
- means for intensity modulating said excitation beam;
- means for focusing said excitation beam onto said sample;
- means for detecting all wavelengths simultaneously; and
- a phase comparator arranged to compare signals from the means for intensity modulating the excitation beam and from the means for detecting all wavelengths simultaneously.

38. The apparatus of claim 37 wherein the means for intensity modulating comprises a modulation driver.

39. An apparatus for use in quantitative analysis of a turbid pharmaceutical sample, comprising:
- means for generating an excitation beam of radiation comprising an array of diode lasers and a multiplexer;
- means for focusing said excitation beam onto said sample;
- means for splitting said excitation beam into two beams; and
- means for detecting transmitted light and non-transmitted light respectively.

* * * * *

UNITED STATES PATENT AND TRADEMARK OFFICE
CERTIFICATE OF CORRECTION

| | |
|---|---|
| PATENT NO. | : 7,105,823 B2 |
| APPLICATION NO. | : 10/472425 |
| DATED | : September 12, 2006 |
| INVENTOR(S) | : Christoffer Abrahamsson et al. |

It is certified that error appears in the above-identified patent and that said Letters Patent is hereby corrected as shown below:

On The Title Page, Item (56)
In the References Cited Section, the "Tsuyoshi" reference, after "applications" insert --to organic--.

Signed and Sealed this

Twenty-eighth Day of August, 2007

JON W. DUDAS
*Director of the United States Patent and Trademark Office*